United States Patent [19]
Sundrehagen

[11] Patent Number: 5,958,717
[45] Date of Patent: Sep. 28, 1999

[54] IMMUNOASSAY FOR HOMOCYSTEINE

[75] Inventor: Erling Sundrehagen, Moss, Norway

[73] Assignee: Axis Biochemicals ASA, Oslo, Norway

[21] Appl. No.: 09/210,479

[22] Filed: Dec. 14, 1998

Related U.S. Application Data

[63] Continuation of application No. 08/256,367, Sep. 14, 1994.

[30] Foreign Application Priority Data

Jan. 22, 1992 [NO] Norway ................................ 920282
Mar. 6, 1992 [GB] United Kingdom ................. 9204922

[51] Int. Cl.$^6$ .............................. C12Q 1/34; C12Q 1/00; C12Q 1/48; C12Q 1/42
[52] U.S. Cl. ................................. 435/18; 435/4; 435/15; 435/21; 435/7.1; 435/16; 435/23; 435/28; 435/24
[58] Field of Search .................. 435/18, 4, 15, 435/21, 7.1, 16, 23, 28, 24

[56] References Cited

U.S. PATENT DOCUMENTS

| | | | |
|---|---|---|---|
| 4,281,061 | 7/1981 | Zuk et al. | 435/18 |
| 4,478,934 | 10/1984 | Sato et al. | 435/18 |
| 5,124,351 | 6/1992 | Rabinovitz et al. | 514/499 |
| 5,385,933 | 1/1995 | Rabinovitz et al. | 435/975 |
| 5,478,729 | 12/1995 | Van Atta et al. | 435/975 |
| 5,631,127 | 5/1997 | Sundrehagen | 435/4 |
| 5,827,645 | 10/1998 | Sundrehagen | 435/4 |

FOREIGN PATENT DOCUMENTS

| | | |
|---|---|---|
| A 0070033 | 1/1983 | European Pat. Off. . |
| A 2549853 | 2/1985 | France . |

OTHER PUBLICATIONS

Bergmeyer, *Methods of Enzymatic Analysis*, 1985, pp. 110–117 and 357–364 and 403–409.

Refsum et al., *Clinical Chemistry*, vol. 31, No. 4, Apr. 1985, pp. 624–628.

Refsum et al., "Radioenzymic Determination of Homocysteine in Plasma and Urine", Clin. Chem. 31(4), pp. 625–628 (1985).

Hemmila, "Fluoroimmunoassays and Immunofluorometric Assays", Clin. Chem. 31/3, pp. 359–370 (1985).

Harlow et al., "Antibodies a Laboratory Manual", Chapter 14, Cold Spring Harbor Laboratory, 1988.

Ueland et al., "Total Homocysteine in Plasma or Serum: Methods and Clinical Applications", Clin. Chem. 39/9, pp. 1764–1779 (1993).

Andersson et al., "Homocysteine and other Thiols determined in Plasma by HPLC and Thiol–Specific Postcolumn Derivatization", Clin. Chem. 39/8, pp. 1590–1597 (1993).

*Primary Examiner*—Louise N. Leary
*Attorney, Agent, or Firm*—Bacon & Thomas

[57] ABSTRACT

The invention relates to a method for assaying homocysteine in a sample such as blood, plasma or urine, which comprises the steps of contacting the sample with a homocystene conveying enzyme and at least one substrate for the enzyme other than homocysteine, and without chromatographic separation, assessing a non-labelled analyte selected from a homotysteine co-substrate and the homocysteine conversion products of the enzymic conversion of homocysteine by said enzyme.

13 Claims, No Drawings

IMMUNOASSAY FOR HOMOCYSTEINE

This application is a Continuation of nonprovisional application Ser. No. 08/256,367 filed Sep. 14, 1994.

The present invention relates to an assay for homocysteine in clinical samples.

Homocysteine is an intermediary amino acid produced when methionine is metabolized to cysteine. Generally, homocysteine produced in the body is rapidly metabolized by one of two routes, (1) condensation with serine to form cystathione or (2) conversion to methionine, and its concentration (and that of its oxidized form homocystine) in the living body under normal conditions is virtually negligible.

Homocysteine levels in biological samples may however be of clinical significance in a number of situations as homocysteine plays an important part in the complex set of pathways which make up sulphydryl amino acid metabolism and its accumulation may be indicative of various disorders occurring in these pathways, including in particular inborn errors of metabolism. Thus, for example homocystinuria (an abnormal build-up of homocysteine in the urine) is known to be a disorder of amino acid metabolism resulting from deficiencies in the enzymes cystathione β synthetase or methyltetrahydrofolic acid methyltransferase (which catalyses the methylation of homocysteine to methionine).

Sulphydryl amino acid metabolism is closely linked to that of folic acid and vitamin $B_{12}$ (cobalamin), which act as substrates or co-factors in the various transformations involved. For this reason homocysteine accumulation has also been proposed as an indicator of malfunction of cobalamin or folate dependent enzymes, or other disorders or diseases related to cobalamin or folate metabolism.

Moreover since homocysteine conversion to methionine relies on a reaction requiring S-methyl tetrahydrofolate as the methyl donor, homocysteine metabolism may also be affected by anti-folate drugs, such as methotrexate, administered to combat other disorders, notably cancer. Monitoring of homocysteine has therefore also been proposed in the management of malignant disease treatment with anti-folate drugs.

More recently, elevated levels of homocysteine in the blood have been correlated with the development of atherosclerosis (see Clarke et al., New Eng. J. Med. 324:1149–1155 (1991)) and even moderate homocysteinemia is now regarded as a risk factor for cardiac and vascular diseases. Measurement of plasma or blood levels of homocysteine is thus also of importance in the diagnosis and treatment of vascular disease.

Although immunological methods of determining homocysteine directly are not available as there is no available antibody to homocysteine, a number of other methods for determining homocysteine in clinical samples have been proposed. These have all involved chromatographic separations and generally have been based on one of the three following principles:

(1) classical chromatographic amino acid analysis,
(2) reaction of homocysteine in the sample with the enzyme S-adenosyl-L-homocysteine hydrolase in the presence of a radioactively or otherwise labelled S-adenosine co-substrate followed by separation and quantitation of the product (S-adenosyl-L-homocysteine, SAH) formed. Generally chromatographic separation (HPLC or TLC) and radioactivity measurements are used (see Refsum et al., Clin. Chem. 31:624–628 (1985); Kredich et al., Anal. Biochem 116:503–510 (1981); Chui, Am. J. Clin. Path. 90(4): 446–449 (1988); Totani et al., Biochem. Soc. 14(6):1172–9 (1988); and Schimizu et al., Biotechnol. Appl. Biochem 8:153–159 (1986))
(3) reaction of homocysteine in the sample with a fluorophore, followed by HPLC-separation and fluorometry (see Refsum et al., Clin. Chem. 35(9); 1921–1927 (1989)).

These methods are time-consuming and cumbersome to perform and all rely on direct quantitation. More particularly, chromatographic separation is a common feature of the prior art methods and requires highly specialized and sophisticated equipment.

The use of such equipment is generally not well accepted in routine clinical laboratory practice and such processes are consequently not generally amenable to automation in typical clinical laboratory procedures.

A need therefore exists for an improved assay for homocysteine which is simple, specific, quick to perform, readily adapted for use in clinical laboratories and above all which avoids the need for costly and time-consuming chromatographic separation. The present invention seeks to provide such an assay.

In one aspect the present invention therefore provides a method for assaying homocysteine in a sample, said method comprising the steps of contacting the sample with a homocysteine converting enzyme, eg. an S-adenosyl homocysteine (SAH) hydrolase, and at least one substrate for said enzyme other than homocysteine, and without chromatographic separation (i.e. of reagents or reaction products) assessing (preferably photometrically) a non-labelled analyte selected from the homocysteine co-substrate and the products of the enzymic conversion of homocysteine by said enzyme.

After contacting the sample with the homocysteine converting enzyme and the substrate, it is preferably incubated for at least 30 seconds, especially at least 5 minutes before the subsequent stages of the assay are performed.

The homocysteine converting enzyme used in the assay of the invention is especially preferably SAH-hydrolase but other enzymes may be used. Thus mention may be made for example of betaine-homocysteine methyl transferase and other enzymes involved in homocysteine conversions, (as described for example by Graham in Trends Cardiovasc. Med. 1: 244–249 (1991)).

The homocysteine co-substrate assessed in the method of the invention is a compound which reacts with homocysteine in the enzyme catalyzed, e.g. a SAH-hydrolase catalyzed, homocysteine conversion reaction.

As used herein the term "assessing" is intended to include both quantitative and qualitative determination in the sense of obtaining an absolute value for the amount or concentration of the analyte, e.g. homocysteine co-substrate, present in the sample, and also obtaining an index, ratio, percentage, visual or other value indicative of the level of analyte in the sample. Assessment may be direct or indirect and the chemical species actually detected need not of course be the analyte itself but may for example be a derivative thereof or some further substance as discussed below.

The assay of the invention conveniently uses either enzymic or immunological techniques for analyte assessment. In one preferred enzymic technique the analyte is contacted with a further enzyme for which it is a substrate and either a co-substrate or a direct or indirect reaction product of the enzymic conversion of the analyte by that further enzyme is assessed. In a preferred immunological technique the analyte is assessed using a procedure involving competitive binding to an antibody by the analyte and a further hapten (e.g. a polyhapten or a labelled analogue of the analyte) and assessment of the bound or unbound hapten.

The preferred homocysteine converting enzyme used according to the invention is S-adenosyl-homocysteine hydrolyze (SAH-hydrolyze) which catalyzes the homocysteine reaction adenosine+homocysteine⇌S-adenosyl-homocysteine (SAH)

a reaction which has an equilibrium constant K of $10^6$ $M^{-1}$.

The reaction may run in either direction, depending on reaction conditions, reactant concentration etc.

In the above scheme, adenosine is the homocysteine co-substrate. Other co-substrates such as adenosine analogues or related compounds however may be used in the assay method of the invention.

The assay of the invention can take particular advantage of the fact that homocysteine acts as an inhibitor of SAH-hydrolase, suppressing the hydrolysis reaction which forms homocysteine and adenosine and pushing the reaction equilibrium in favor of SAH synthesis.

The amount of homocysteine in a sample thus indirectly influences the formation or consumption of the homocysteine co-substrate, e.g. adenosine, by SAH-hydrolase and thereby its resulting concentration in the reaction mixture. In this invention the resulting concentration, or change in the concentration of homocysteine co-substrate, e.g. adenosine, in the reaction mixture can be used as an indicator for the initial concentration of homocysteine in the sample. Thus where the analyte is the co-substrate the assay of the invention differs from prior art methods in that, rather than being assessed directly, homocysteine is assessed indirectly by determining the concentration of its co-substrate in its enzyme catalyzed conversion. This has the direct advantage that detection methods which are suited to typical clinical laboratory procedures but which were not usable in the prior art assays for homocysteine, e.g. photometric methods, may be used so making the assay according to the invention particularly suited for routine clinical use.

In the preferred assay method of the invention, the SAH-hydrolase reaction may be used in either direction. Thus if the test sample is contacted with adenosine and SAH-hydrolase, an amount of adenosine is consumed which corresponds to the amount of homocysteine consumed, and the amount of homocysteine in the sample can thus be determined from the alteration in the adenosine concentration. Adenosine analogues and/or adenosine generating compounds may be used in the place of adenosine itself.

In other preferred embodiments of the invention, the opposite direction of reaction may be used. The test sample may be contacted with SAH (generally in excess) and SAH-hydrolase. Homocysteine and adenosine are then formed from hydrolysis of the SAH. Any homocysteine present in the test sample will counteract this net reaction, and thus inhibit the formation of adenosine, the amount of which is monitored.

The SAH-hydrolase substrates used in the method of the invention may thus be SAH or adenosine or analogues and precursors thereof.

Many enzymes are involved in the complex series of pathways of sulphydryl amino acid metabolism and transmethylation reactions in the body. These pathways and reactions have been well studied and the regulatory roles of the enzymes concerned investigated. The role of one such enzyme, SAH-hydrolase, is discussed in a review by Ueland in Pharmacological Reviews 34: 223–253 (1982). Trewyn et al., in J. Biochem. Biophys. Met. 4: 299–307 (1981), describe an investigation into the regulatory role of SAH-hydrolase and provide an assay for SAH-hydrolase enzymatic activity. Garras et al. in Analytical Biochem. 199: 112–118 (1991) described other homocysteine reaction pathways and in particular provide an assay for the methionine synthase mediated conversion of homocysteine. As mentioned earlier, Graham (Supra) describes further enzyme mediated homocysteine conversions. The co-substrates and the conversion products of these various reactions may be used as the analytes in the assay of the invention, especially where an immunological means of assessment is employed.

Clinical samples to be assayed according to the invention may be derived from any biological fluid or tissue extract and may be pretreated prior to assay. Plasma or urine samples will however generally be used.

In the plasma or urine, significant proportions of the homocysteine present may be bound by disulphide linkage to circulating proteins, such as albumin, and homocysteine may also be present in the form of other disulphide derivatives (generally homocysteine-cysteine conjugates). To obtain an estimate of total homocysteine present in the sample it may therefore be desirable to treat the sample with a reducing agent to cleave the disulphide bonds and liberate free homocysteine.

Disulphides are easily and specifically reduced by thiols (e.g. dithiothreitol (DTT), dithioerythritol (DTE), 2-mercapto-ethanol, cysteine-thioglycolate, thioglycolic acid, glutathione and similar compounds). Direct chemical reduction can be achieved using borohydrides (e.g. sodium borohydride) or amalgams (e.g. sodium amalgam) or more specialized reagents such as phosphines or phosphorothioates can be used. Disulphide reduction is reviewed by Jocelyn in Methods of Enzymology 143: 243–256 (1987) where a wide range of suitable reducing agents is listed.

Adenosine or the other homocysteine co-substrates may be assessed by known methods. Generally methods relying upon photometric (e.g. colorimetric, spectrophotometric or fluorometric) detection and immunological methods are preferred as these may particularly readily be adapted for use in clinical laboratories. Methods based on enzymic reaction or reaction with mono- or polyclonal antibodies are particularly preferred, as these are simple and quick and can be relatively inexpensive to perform. Thus for example the analyte may be assessed by monitoring the reaction with enzymes which convert it directly or indirectly to products which may be detected photometrically, e.g. spectrophotometrically. Suitable enzymes, which should of course be non-reactive with the other substrates of the homocysteine converting enzyme, particularly homocysteine, include adenosine deaminase (which converts adenosine to inosine) and adenosine kinase (which converts adenosine and ATP to ADP and phosphorylated adenosine). Such enzymes may further be combined with other enzymes which act to convert the products formed to further detectable products.

Examples of immunological methods would include methods involving reaction of the analyte with antibodies specific for it which either are themselves assessable or which can be reacted further to form detectable products, eg. in a sandwich assay. One particularly attractive immunological method however involves the use of a fluorophore labelled analogue of the analyte, preferably a co-substrate, eg. fluorescein labelled adenosine—this and the unlabelled analyte may be contacted with an antibody for the analyte. If the resultant product is subjected to a fluorescence polarization assay using polarized exciting radiation an indication of the unlabelled analyte concentration may then be derived from the degree of depolarization of the fluorescence radiation. Adenosine antibodies are commercially available (eg. from Paessel & Lorei GmbH, Frankfurt, Germany and Serotech Ltd., Oxford, United Kingdom) and fluorescence polarization immunoassay (FPIA) techniques are well established (see for example U.S. Pat. No. 4,420,568 and U.S. Pat. No. 4,593,089 and other publications by Abbott Laboratories relating to their TDx technology).

Thus examples of detection schemes useful in the assay of the invention include

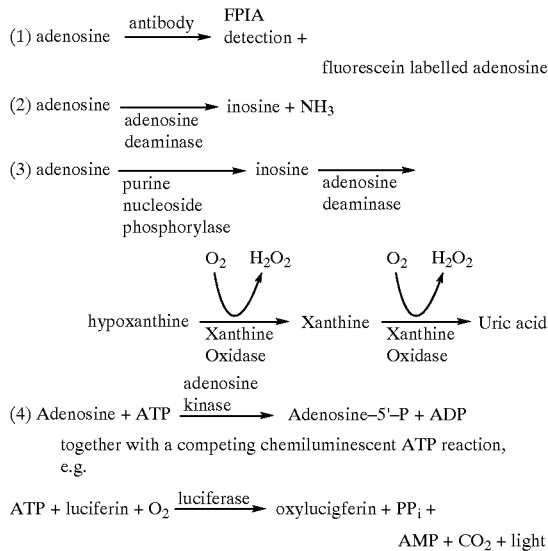

or with a fluorophore labelled adenosine which competes for the ATP/adenosine kinase, with assessment being performed by fluorescence polarization measurement.

As regards schemes (2) and (3), inosine and uric acid have distinctive UV absorption properties and can thus be monitored spectrophotometrically, by kinetic measurements.

However the use of UV detection of uric acid or inosine has certain limitations in that the sensitivity of the method is rather poor and it requires a UV-light source and a UV-transparent sample container. It may thus be more convenient to rely upon calorimetric detection or electronic sensors, and such methods, particularly colorimetry, are generally favored in clinical laboratories.

In this connection the reaction of scheme (2) is particularly useful in that ammonia generated by the adenosine deaminase reaction may readily be detected using known colorimetric techniques. Thus for example ammonia generated in the sample may be reacted to form coloured products, the formation of which may be detected spectrophotometrically. One such method, described in Methods of Enzymatic Analysis (Bergmeyer) Volume 1:1049–1056 (1970) relies upon the reaction of ammonia with phenol in the presence of hypochlorite in alkaline conditions to form the coloured dye indophenol:

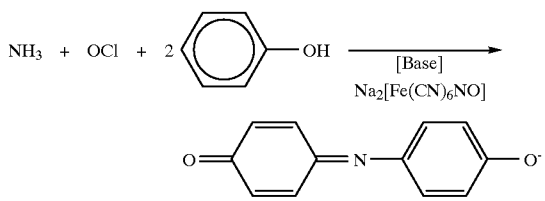

Sodium nitroprusside may be used as catalyst. Modifications of the method using for example various derivatives of phenol may also be used.

The coloured end-product is formed in amounts directly proportional to the concentration of ammonia, and hence adenosine, in the sample.

In scheme (3), the xanthine oxidase reaction lends itself to detection using fluorogens or chromogens, e.g. red-ox indicators, by assessing the reduction/oxidation potential, or by measuring $O_2$ consumption, or more particularly $H_2O_2$ formation, for example by the use of electronic sensors. Numerous red-ox indicators can be used for this purpose, and a wide range of methods are described in the literature for assaying $H_2O_2$ and $O_2$ in solution. Indeed, $H_2O_2$ is frequently detected in clinical assays.

Suitable red-ox indicators include methylene blue, 2,6-dichlorophenol, indophenol and the various red-ox indicators listed in Table 1 of the Kodak Laboratory & Research Products, catalog No. 53, although others may of course be used. Enzymes with peroxidase activity, e.g. horseradish peroxidase, may be added to facilitate the red-ox reactions.

If a precipitating chromogen is desired, MTT tetrazolium may be used in combination with xanthine oxidase or other similar enzymes. By the use of a precipitating chromogen or fluorogen, a reading of immobilized colour or fluorescence can be obtained to obtain a visual indication of homocysteine concentration.

In scheme (4), a chemiluminescent ATP reaction is used to assess adenosine concentration. Chemiluminescence based assays have great potential due to the low detection limits achievable and to the relative simplicity of the necessary instrumentation. Chemiluminescent reactions can be used to detect analytes such as ATP or $H_2O_2$ and one of the most efficient and best known such reactions is the firefly bioluminescence reaction

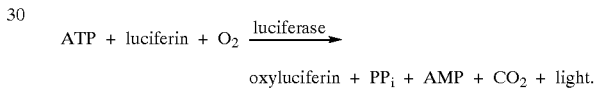

Firefly luciferin has a benzothiazole structure but luciferins from other biological sources are available which have other structures. For analytical purposes ATP, luciferin or luciferase could be assayed directly using this reaction. Another chemiluminescent reaction which could be used where $H_2O_2$ is generated, as for example in scheme (3), is the luminol reaction (luminol is 5-amino-2,3-dihydrophthalazine-1,4-dione) with hydrogen peroxidase catalyst which results in light emission at 425 nm.

Hydrogen peroxide, from scheme (3) for example, can also be assessed using the non enzymic chemiluminescent reactions of peroxioxalate and the acridinium esters, the latter in aqueous solution at neutral pH.

The use of fluorophore labelled adenosine in scheme (4) and assessment by fluorescence polarization measurement is feasible due to the relatively broad substrate specificity of adenosine kinase. This broad specificity can moreover be used to compensate for endogenous adenosine (or other adenosine kinease nucleoside substrates) by adding adenosine kinase to the sample as a pretreatment, preferably in combination with the reducing agent (e.g. DTT).

Such enzymic pretreatment of the sample is desirable as, in many of the embodiments of the invention, the analyte (e.g. adenosine) is already present in the sample in varying amounts, thus providing a potential source of error in the assay. Background analyte content can be compensated for by running the assay on a portion of the sample without using the homocysteine converting enzyme (e.g. SAH-hydrolase); however such a procedure is time consuming and makes the assay more cumbersome. An alternative is pre-treatment of the sample with an agent serving to convert or remove the endogenous analyte, e.g. an enzyme such as adenosine kinase or adenosine deaminase which removes the background adenosine. As mentioned above, to avoid unnecessarily increasing the time required for the assay to be run, such treatment of the sample may conveniently be effected at the time that it is pre-treated with the reducing agent to liberate the homocysteine.

Besides the use of spectrometric or calorimetric techniques for analyte assessment, other photometric techniques may be used. Among the most useful techniques that can be used are particle agglutination and immunoprecipitation techniques. If polyclonal antibodies are used, direct particle agglutination or direct immunoprecipitation may be used, although where SAH-hydrolase is used as the homocysteine converting enzyme this will generally not be preferred. However precipitation inhibition or particle agglutination inhibition techniques can be used. These rely on the use of antibody/hapten combinations which on conjugation lead to precipitation or particle aggregation which can be detected by turbidimetric or nephelometric measurement. Where the antibody/hapten complex formation is inhibited by the analyte, e.g. SAH, the SAH content may be assessed from the reduction in precipitation/aggregation. The reaction can be expressed as follows

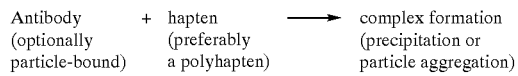

| Antibody | + | hapten | → | complex formation |
| (optionally | | (preferably | | (precipitation or |
| particle-bound) | | a polyhapten) | | particle aggregation) |

Where the assay of the invention is effected using SAH-hydrolase as the homocysteine converting enzyme, it is advantageous either to store the SAH-hydrolase in the presence of a reducing agent or to treat it with a reducing agent prior to its use in the assay. It has been found that storage otherwise causes SAH-hydrolase to become inactivated and this use of a reducing agent either prevents inactivation during storage or causes reactivation prior to use.

Various reducing reagents can be used (for example DTT, cysteine, mercaptoethanol, dithioerythritol, sodium borohydride, etc.), however DTT is particularly suitable, e.g. at about 5 mM concentration. DTT should itself be stored at low pH and thus the assay kit can conveniently include a solution of DTT at a low pH (e.g. about 3) but with a low buffer capacity and a separate solution of SAH-hydrolase, which may be partially or totally inactive, at substantially neutral pH and preferably buffered. When these solutions are combined, the enzyme is reactivated at neutral pH. This combination can if desired take place in the presence of the test sample, or with the test sample added shortly thereafter, so that the homocysteine liberation is effected simultaneously. The other reducing agents mentioned above may similarly be used for both SAH-hydrolase stabilization/activation and for reducing the sample to liberate homocysteine.

The use of reducing agents to reactivate inactivated SAH-hydrolase forms a further aspect of the invention. Moreover in a still further aspect the invention also provides a kit comprising in a first compartment an inactive SAH-hydrolase and in a second compartment a reducing agent, e.g. DTT in an acid medium (for example pH 3). Using this kit the SAH-hydrolase can be mixed with the reducing agent, and so reactivated, immediately prior to its use in the assay.

Other additives may advantageously be used to enhance SAH-hydrolase stability during storage or in the assay itself. These include NAD⁺, glutathione, polyhydric alcohols and sugars (e.g. inositol, sorbitol, xylitol, eryrthritol, glycerol, ethylene glycol, sucrose, lactitol, etc.), soluble polymers such as certain dextrans, and proteins (e.g. carrier proteins).

Where the assay of the invention uses antibodies, these may be polyclonal but preferably are monoclonal. Where the desired antibodies are not already commercially available, they may be produced by standard techniques. Antibodies can thus be raised in animals or hybridomas, either monoclonal or polyclonal, e.g. as described by James Gooding in "Monoclonal antibodies, principle and practice", Academic Press, London, 1983, Chapter 3. Monoclones must be sorted to select clones which discriminate between the desired hapten and other substrates for the enzyme(s), e.g. which discriminate between adenosine and SAH. Polyclonal antibodies reactive only with the analyte (e.g. SAH) should be purified to remove cross-reacting antibodies, i.e. those reactive with other substrates besides the analyte, e.g. with both adenosine and SAH. This can be done by affinity chromatography, e.g. where SAH is the analyte by using immobilized adenosine.

In the production of the antibody one uses as a hapten either the analyte itself or another molecule which includes the portion of the analyte that is considered to be the most appropriate binding region, e.g. a region remote from those regions participating in the enzymic reaction. The hapten is conveniently conjugated to a macromolecule such as BSA or hemocyanin. For SAH, the desired epitope is preferably at or about the thioether bridge and thus while one can use SAH itself

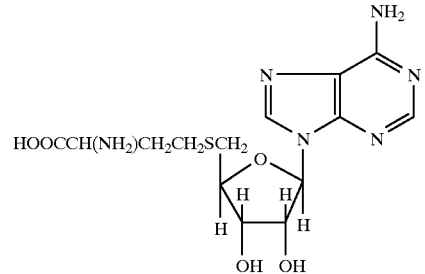

conjugated to a macromolecule, it is preferred to use a "simplified" molecule such as one of formula (I)

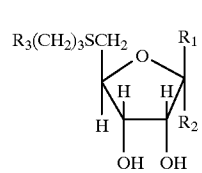

(I)

(where $R_1$ and $R_2$ which may be the same or different are hydrogen atoms or $OR_4$ groups (wherein $R_4$ is a lower (e.g. $C_{1-6}$, especially $C_{1-4}$) aliphatic group such as an alkyl group, preferably a methyl or ethyl group) or $R_1$ and $R_2$ together represent an oxygen atom, and $R_3$ is an amine or carboxyl moiety) or a salt or ester (e.g. with a $C_{1-4}$ alkanol) thereof, again coupled to a macromolecule.

Examples of compounds of formula I that may be used as haptens thus include

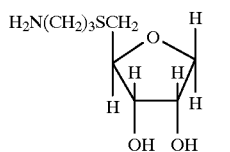

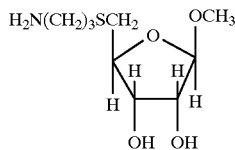

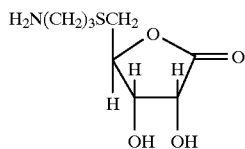

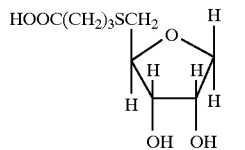

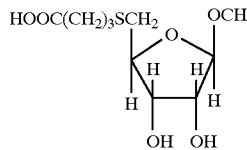

and

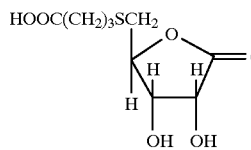

Such "simplified" structures may also be adopted for the labelled analogues mentioned above used in assays where the analyte and labelled analogue are involved in a competitive binding reaction with the antibody. Thus the signal giving moiety R*, which may be selected from fluorophores, chromophores, radiolabels, enzymic, chemiluminescent and other lables conventionally used in immunoassays can be conjugated to the analyte, as for example R*-SAH, or to a simplified, epitope containing molecule as for example

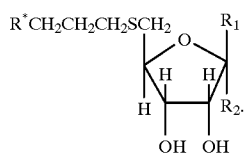

Such labelled moieties can of course be coupled to particles, polymers, proteins or other materials if desired.

The labelled furanose 6-thioethers and the compounds of formula I are novel and form further aspects of the invention.

Viewed from a further aspect the invention provides a process for the preparation of a compound of formula I, said process comprising at least one of the following steps:

(a) reacting a compound of formula II

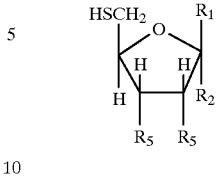

(II)

(wherein $R_1$ and $R_2$ are as defined above and each $R_5$ is a protected hydroxyl group or both $R_5$ together are an alkylenedioxy group (i.e. a protected bis hydroxy group, such as —OC(CH$_3$)$_2$O—) with a propyl halide of formula III $$R_6(CH_2)_3Hal \quad (III)$$

(where $R_6$ is an $R_3$ group or a protected $R_3$ group and Hal is a halogen atom, e.g. a bromine atom) followed by removal of any protecting groups if desired;

(b) (to produce a compound of formula I wherein $R_3$ is an amino group) reacting a compound of formula II with acrylonitrile and reducing and deprotecting the cyano propyl thio-ether product obtained; and (c) esterifying a compound of formula I wherein $R_3$ is a carboxyl group.

The starting products of formula III can be produced by standard techniques or are known from the literature. The starting products of formula II may be produced from the corresponding 1-hydroxymethyl furanoses by cis-hydroxy group protection, bromination and subsequent reaction with thiourea and hydrolysis. The 1-hydroxymethyl-furanoses may be cis-hydroxy group protected by reaction with conventional hydroxy-protecting agents, e.g. acetone.

Examples of reaction schemes for the preparation of compounds of formula I include the following (compounds (1) and (3) are commercially available)

(A)

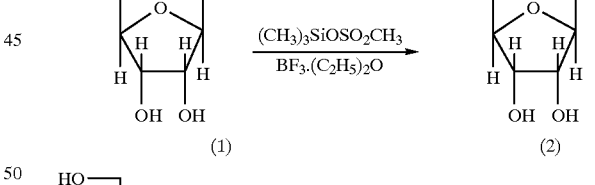

(B)

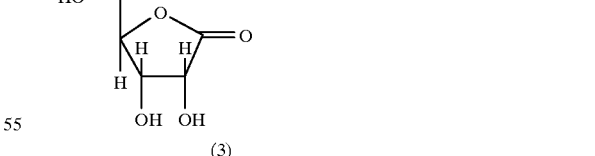

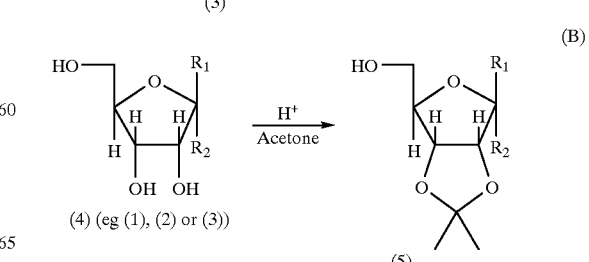

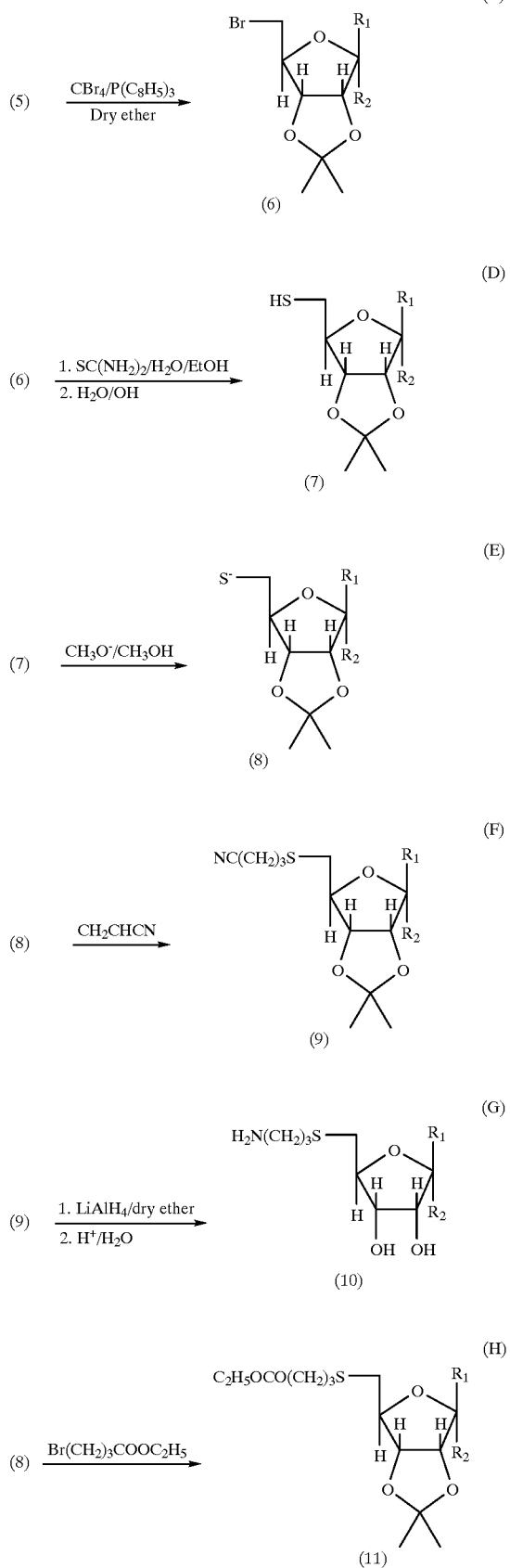

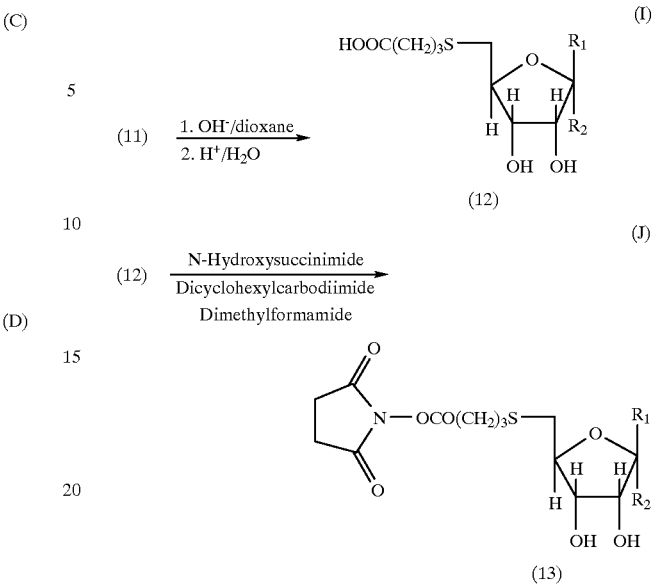

UV absorption, absorption of visible light, or fluorescence by substances in the reaction mixture, optionally precipitated or otherwise separated from the reaction mixture, may be measured at the reaction end point (when the signal is stable) or at one or more fixed time points or alternatively a kinetic measurement may be adopted in which several measurements are made at different points of time.

To perform the assay of the invention, the necessary reagents may be added to the reaction mixture in a sequential manner or simultaneously. However, in many preferred embodiments, one or more of the reactions may advantageously be run for some time before the addition of reagents for the subsequent reaction(s). As an example, where the test sample is reacted with adenosine and SAH hydrolase, the formation of SAH from homocysteine and adenosine is preferably allowed to take place for some time before the adenosine assessment procedure is initiated.

In clinical chemistry analysis, the use of standard curves for calibration purposes is standard practice. Thus, in the performance of the method of this invention, samples of known homocysteine content may be used in the place of clinical samples to construct a standard curve for the response/signal to be measured and the homocysteine content of the unknown samples may then be calculated by interpolation from the standard curve. Thus an exact quantification of the signal forming molecules or the red-ox potentials is not necessary.

The assay method of the present invention may be used for the diagnosis and monitoring of pathological or potentially pathological conditions which are related to or manifested in the homocysteine content of body fluids or tissues. These include atherosclerosis, blood diseases, vitamin deficiencies and/or inborn errors of metabolism. It may also be used for the evaluation of the effects of pharmaceuticals, such as anti-folate drugs.

In another aspect the invention provides an analytical product, optionally in kit format, for use in the assay of homocysteine in a sample, said product comprising: a homocysteine converting enzyme; a substrate for said enzyme other than homocysteine; a signal forming agent; and, optionally, means for signal assessment.

In one preferred embodiment, the analytical product comprises: a homocysteine converting enzyme, eg. S-adenosylhomocysteine hydrolase; one or more substrates for said enzyme other than homocysteine; means for generating a detectable derivative of an analyte selected from the homocysteine co-substrate and the products of the enzymic conversion of homocysteine; and, optionally, means for spectrometrically or calorimetrically assessing said detectable derivative to provide an indication of the homocysteine content of the sample.

In another embodiment, the product comprises: adenosine; S-adenosyl-homocysteine hydrolase; an adenosine converting enzyme; optionally, a co-substrate for said adenosine converting enzyme; and means for generating a photometrically detectable response from said co-substrate or from a product of enzymic conversion of adenosine by said adenosine converting enzyme. Thus for example the adenosine converting enzyme may be adenosine kinase and the means for generating may comprise ATP, luciferin and a luciferase. Alternatively, the adenosine converting enzyme may be adenosine deaminase and the means for converting may comprise nucleoside phosphorylase, xanthine oxidase and a peroxidase.

In a still further embodiment the kit comprises adenosine; S-adenosyl-homocysteine; an optionally matrix particle bound anti-S-adenosyl-homocysteine antibody; a polyhapten for said antibody; and, optionally, means for photometrically assessing agglutination or precipitation of antibody-:polyhapten complexes. In this embodiment, the polyhapten may conveniently be provided by a backbone polymer to which are conjugated a plurality of furanose 6-thioethers, e.g. leaving pendent residues of formula

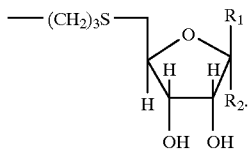

These may be produced for example by reacting a carboxylic acid of formula I (or an anhydride or acid halide thereof) with a polymer having a plurality of pendant amines (e.g. polylysine) or an amine of formula I with a polymer having pendent carboxyl groups.

In the kits, all or some of the reagents may be present in dry form, as may the format/matrix for processing the reactions of the reaction mixture. Similarly the kit may, as indicated, include, as means for assessing a detectable analyte or derivative, relatively inexpensive spectrometric or calorimetric apparatus, e.g. a light source and detector arrangement preset to detect light intensity at a wavelength characteristic of the detectable analyte, etc. or even a simple calorimetric calibration chart.

The invention will now be described by means of the following non-limiting Examples. The assay of Example 19 is especially preferred.

EXAMPLE 1

The sample (an aqueous homocysteine solution for calibration or plasma or urine for clinical assay) was pretreated with a reducing agent (e.g. 10 mM dithiothreitol). This sample was added, preferably to a final concentration of homocysteine in the range $10^{-6}$–$10^{-5}$ mol/l, to a solution at 37° C. comprising rabbit IgG 5 mg/ml, adenosine deaminase 20 mU/ml, nucleoside phosphorylase 20 mU/ml, xanthine oxidase 20 mU/ml, horseradish peroxidase 500 mU/ml, 10 mmol/l dithiothreitol, 100 mmol/l sodium phosphate, pH adjusted to 7.40, and 100 mU S-adenosyl-1-homocysteine hydrolase. Either simultaneously or subsequently, but preferably after 10 minutes incubation to allow conversion of adenosine within the sample, adenosine was added to a final concentration of $5.10^{-6}$ mol/l. UV absorption was measured during a 10 minute period and the response was measured at 292 nm in a kinetic mode, and the $\Delta A/\Delta t$ was calculated.

For clinical tests the homocysteine concentration may be calculated by interpolation into a standard curve produced using the known standards.

EXAMPLE 2

The sample (as for Example 1) was pretreated with a reducing agent (e.g. 10 mM dithiothreitol). This sample was added, preferably to a final concentration of homocysteine in the range $10^{-6}$–$10^{-5}$ mol/l, to a solution at 37° C. comprising rabbit IgG 5 mg/ml, adenosine deaminase 20 mU/ml, xanthine oxidase 20 mU/ml, nucleoside phosphorylase 20 mU/ml, horseradish peroxidase 500 mU/ml, 10 mmol/l dithiothreitol and 100 mmol/l sodium phosphate, pH adjusted to 7.40, 20 mU S-adenosyl-1-homocysteine hydrolase. Then, preferably after 10 minutes incubation to allow conversion of adenosine within the sample to occur, S-adenosyl-1-homocysteine was added to a final concentration of $5.10^{-5}$ mol/l, and the UV absorption was measured during a 10 minute period. At 292 nm in a kinetic mode, the $$\frac{\Delta A}{\Delta t}$$

was calculated.

For clinical tests the homocysteine concentration may be calculated by interpolation into a standard curve produced using the known standards.

EXAMPLE 3

Assay Buffer 0.1 M phosphate buffer pH 7.4, comprising 1 mg/ml rabbit IgG and 10 mmol/l dithiothreitol.

Assay Procedure

To 150 µl assay buffer, 3 mU S-adenosyl-1-homocysteine hydrolase and sample (preferably pretreated as described in Examples 1 and 2) were added. The enzyme reaction was started by addition of adenosine dissolved in assay buffer, to a final concentration of $2.5\times10^{-5}$ mol/l. After 10 minutes incubation, 750 µl of a solution of assay buffer comprising 20 mU adenosine deaminase, 20 mU nucleoside phosphorylase, 20 mU xanthine oxidase and 375 mU of horseradish peroxidase were added. The UV absorption at 292 nm was measured for 5 minutes in a kinetic mode. The $$\frac{\Delta A}{\Delta t}$$

is calculated. In parallel, the assay is repeated but without the addition of S-adenosyl-1-homocysteine hydrolase. The difference between the two values of $$\frac{\Delta A}{\Delta t}$$

is determined and the homocysteine concentration is calculated by interpolation into a standard curve.

EXAMPLE 4

The assay procedure is performed as described in Example 3 up to the first incubation. Then, after 10 minutes incubation, an assay solution comprising fluorescein-labelled adenosine and monoclonal anti-adenosine antibodies is added. The remaining adenosine and the fluorescein labelled adenosine compete for binding to the antibody. The amount of labelled adenosine bound to the antibodies is assessed by the conventional fluorescence polarization technique, and the homocysteine concentration is calculated by interpolation into a standard curve.

EXAMPLE 5

Assay Buffer
0.1 M phosphate buffer pH 7.4, comprising 1 mg/ml rabbit IgG and 10 mmol/l dithiothreitol.

SAH-hydrolase Solution
40 mU/ml S-adenosyl-1-homocysteine-hydrolase are dissolved in the assay buffer.

Adenosine Solution
$5 \times 10^{-8}$ mol/ml adenosine are dissolved in the assay buffer.

Adenosine Deaminase Solution
200 mU/ml adenosine deaminase dissolved in the assay buffer.

Phenol/nitroprusside Solution
10 mg/ml phenol and 50 µg/ml sodium nitroprusside in water.

Hypochlorite Solution
11 mmol/l NaOCl is dissolved in 125 mM NaOH.

Assay Procedure
1. 75 µl of the adenosine solution and 75 µl of the SAH-hydrolase solution are mixed with the sample (preferably pretreated as described in Examples 1 to 4), and kept at 37° C. for 10 minutes.
2. 100 µl of adenosine deaminase solution is added, and the mixture is kept at 37° C. for 5 minutes.
3. 750 µl of phenol/nitroprusside solution and 750 µl hypochlorite solution is added. After 30 minutes in 37° C., the extinction at 628 nm is measured. In parallel the assay is repeated but without the addition of SAH-hydrolase. The difference between the two values for extinction at 628 nm is determined and the homocysteine concentration is calculated by interpolation of this difference into a standard curve produced using known standards.

EXAMPLE 6

Formation of Fluorophore-labelled SAH

A 10 mmol/l solution of SAH in dimethylformamide is prepared and then diluted 1:10 in a 100 mmol/l phosphate buffer pH=7.5. To this solution fluorescein isothiocyanate is added to a final concentration of 1 mmol/l. After 60 minutes incubation at ambient temperature, the SAH-fluorescein conjugate is purified by HPLC using a Chromasil C-18 column at 260 nm using a gradient mixture of 25 mM ammonium acetate (pH 7.0) and methanol.

EXAMPLE 7

Formation of Anti-SAH-antibodies a) Formation of antigen: To a 1 mmol/l solution of SAH in 25 mmol/l phoshpate buffer pH=7.4, with 125 mmol/l NaCl, bovine serum albumin is added to a final concentration of 5 mg/ml. To this mixture, bis(sulfosuccinimidyl) suberate is added to a final concentration of 1 mmol/l, and the mixture is left to react for 60 minutes. (The pH is kept low in this conjugation reaction to stimulate conjugation at the adenosyl amine rather than at the homocysteine amine function). The proteinaceous fraction of the solution—which also comprises the conjugates between BSA and SAH—is isolated by size exclusion chromatography using a Pharmacia Superose 12 column with phosphate buffered saline as eluant.

b) Formation of hybridomas: With the antigen described, hybridomas are formed according to the procedure described by James W. Gooding in "Monoclonal antibodies: Principle and Practice", Academic Press, London, 1983, Chapter 3.

c) Selection of Hybridomas (i) Hybridomas producing anti-SAH-antibodies are identified as follows: The IgG content of the supernate of the hybridomas is measured by conventional ELISA technique. Then supernate is mixed in a cuvette with a buffer comprising 50 mmol/l phosphate, 120 mmol/l NaCl, pH=7.4, and 0.1 mg rabbit IgG per ml, to a final concentration of 0.1 µmol/l mouse IgG. Fluorescein labelled SAH, formed according to Example 6 above, is added to a final concentration of 0.02 µmol/l. After 10 minutes incubation, the degree of polarization is measured and with a spectrofluorometer equipped with a fluorescence polarization unit by measuring A=the fluorescence intensity when the plane of polarization of incident light is parallel to the polarization plane of the filter used for filtration of the emitted light, B=the fluorescence intensity when the plane of the polarization of incident light is perpendicular to the polarization plane of the filter used for filtration of the emitted light, and using an excitation wavelength of 494 nm and detecting the emitted light at 517 nm.

The degree of polarization is calculated as $(A-B)/(A+B)$

A low degree of polarization indicates that the monoclonal mouse antibodies do not bind SAH.

(ii) From the hybridomas selected according to (i), the hybridomas producing antibodies reactive to adenosine and/or homocysteine are identified as follows: Monoclonal anti-SAH-antibodies from the hybridoma supernate is coated onto microtitre well surfaces as described in Example 9 below. Carbon-14 labelled adenosine (or carbon-14 labelled homocysteine), available from Amersham Ltd, UK, in a buffer comprising 25 mmol/l phosphate, 120 mmol/l NaCl and 1 mg/ml of rabbig IgG and having pH=7.4 is added to the microtitre wells. After 60 minutes incubation, the wells are washed 3 times with the same buffer (not of course containing the adenosine or homocysteine). High values of radioactivity retained in the wells indicate that the hybridomas produce antibodies which bind to adenosine (or homocysteine) on its own. These antibodies are not used in the assay.

(iii) Production of monoclonal IgG: Hybridomas which produce antibodies which bind to SAH according to (i) above but which do not bind to adenosine or homocysteine according to (ii) above are selected for monoclonal IgG production. The hybridomas selected are used for production of ascites in mice or production of cell cultures in vitro, according to conventional techniques. The monoclonal antibodies are furthermore isolated from the ascites or cell culture media according to conventional techniques. See James W. Gooding "Monoclonal antibodies: Principle and practice", Academic Press, London, 1983.

EXAMPLE 8

Fluorescence Polarization Immunoassay of L-homocysteine

Enzyme solution: 50 mmol/l phosphate buffer pH=7.4 comprising 0.2 mg/ml rabbit IgG, 120 mmol/l NaCl, 10 mmol/l dithiothreitol, 10 U/l S-adenosyl-1-homocysteine-hydrolase and 0.1 mmol/l adenosine.

Fluorescein-labelled SAH solution: SAH conjugated with fluorescein, formed according to Example 6, is dissolved to a final concentration of 1 µmol/l in 50 mmol/l phosphate buffer pH=7.4 with 125 mmol/l NaCl and 0.2 mg/ml rabbit IgG.

Antibody solution: Monoclonal anti-SAH antibodies (not reactive with adenosine and preferably also not reactive with homocysteine), e.g. formed according to Example 7, dissolved to a final concentration of 0.1 µmol/l in 50 mmol/l phosphate buffer pH=7.4 with 125 mmol/l NaCl and 0.2 mg/ml rabbit IgG.

Assay performance: In a cuvette, 15 µl plasma (initially a series of samples of known homocysteine content) is mixed with 100 µl enzyme solution and kept at 37 degrees Celsius for 15 minutes. 100 µl of the solution of fluorescein-labelled SAH is added, followed by the addition of 1.0 ml of the antibody solution. With a spectrofluorometer equipped with a fluorescence polarization unit, the degree of polarization is measured as described in Example 7(c)(i) above and is plotted against the homocysteine concentration.

The assay can also be performed using the labelled haptens and antibodies of Examples 11 and 13 or 15 and 17 in place of those of Examples 6 and 7.

EXAMPLE 9

Microtitre Enzyme-linked Immunoassay (a) The enzyme solution of Example 8 is used.

(b) Solution of peroxidase-labelled SAH: 0.5 mg horse-radish peroxidase is dissolved in 1 ml purified water. 200 Al of a solution of 0.02 mol/l sodium periodate is added, the mixture is stirred for 20 minutes at ambient temperature, and dialyzed overnight against a 10 mM sodium acetate buffer pH=4.4. SAH is added to a final concentration of 0.1 mmol/l and the pH is adjusted to 6.0. The solution is stirred for 4 hours at ambient temperature. 100 µl of freshly prepared 4 mg/ml aqueous solution of sodium borohydride is added, and the solution is incubated at 4 degrees Celsius for 2 hours. The peroxidase and its SAH conjugates are isolated by size exclusion chromatography in a column of Superose 6 (Pharmacia, Sweden).

(c) Anti-SAH-antibodies coated on microtitre wells: Polyclonal sheep IgG, from sheep immunized to mouse IgG, is dissolved to a final concentration of 1 mg/ml in 100 mmol/l borate buffer pH=9.0. 300 µl of this solution is filled in each of the wells of polystyrene microtitre plates. After 120 minutes incubation at 37 degrees Celsius, the wells are washed 5 times with phosphate buffered saline. Thereafter, monoclonal mouse IgG anti-SAH-antibodies formed according to Example 7 above, are dissolved in phosphate buffered saline to a final concentration of 50 µg/ml. 200 µl of this monoclonal IgG solution is added to each well and incubated for 120 minutes at 37 degrees Celsius. The wells are then washed 5 times with phosphate buffered saline solution containing 0.1 mg/ml of rabbig IgG.

(d) Assay Performance A 25 µl plasma sample (initially a series of samples of known homocysteine concentration) is mixed with 500 µl of the enzyme solution and kept at 37 degrees Celsius for 15 minutes. 50 µl of the peroxidase-labelled SAH solution is added, and, following mixing, 250 µl of this mixture is added to a well in the anti-SAH-antibody coated microtitre wells produced according to (c) above all buffered to pH 7.4. After 60 minutes incubation at 37 degrees Celsius, the wells are washed three times with phosphate buffered saline containing 0.1 mg/ml rabbit IgG. 100 µl of a 1 mg/ml solution of ortho-phenylenediamine in a 0.1 mol/l citrate buffer pH=6.0 containing 0.015% hydrogen peroxide is added to each well. After 10–30 minutes the light absorbance of each well is read at 450 nm. The absorbance is plotted against the homocysteine concentration.

EXAMPLE 10

Hapten Production

3-S-(1-Anhydro-D-ribofuranosyl)-thiopropyl amine

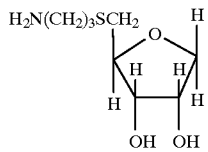

(a) Activated Hydroxy-Protected Mercaptan (Compound (8) in Scheme (E) above)

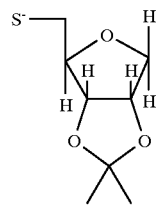

One equivalent of methyl β-D-ribofuranoside (Compound (1) above which is commercially available) is reacted with a mixture of 5 equivalents of trimethylsilylmethane sulphonate and one equivalent of boron trifluoride etherate using the procedure of Jun et al. (Carb. Res. 163: 247–261 (1987)). 0.5 equivalents of the 1-anhydro-D-ribose product (Compound (2)) is added in finely powdered form, in small portions, under continuous stirring to an acetone/sulphuric acid mixture produced by adding 6.3 ml of concentrated sulphuric acid slowly to 100 ml of freshly distilled acetone in an ice bath. The ice bath is removed and reaction is allowed to continue at ambient temperature for 8 hours. The solid white crystalline mass obtained is dissolved in chloroform, washed with aqueous sodium hydroxide, dilute hydrochloric acid and finally water, dried and evaporated down to yield the 2,3-isopropylidene-D-ribonic derivative of 1-anhydro-D-ribose (Compound (2)). One equivalent of this and two equivalents of carbon tetrabromide are dissolved in dry ether and cooled on ice. With constant stirring and cooling on ice, two equivalents of triphenylphosphine are added slowly. The ice bath is removed and the mixture is allowed to warm up to ambient temperature letting the reaction take place and causing hydrogen bromide to evolve smoothly. After the reaction is complete, excess reagent is quenched with the addition of methanol. The bromide derivative (Compound (6)) is isolated by filtration and evaporation down of the filtrate. To the bromide derivative is added thiourea (one equivalent) dissolved in warm water and diluted with rectified spirit. The mixture is refluxed and shaken well periodically, this continuing until about 30 minutes after the bromide derivative dissolves. The reaction mixture is cooled on ice and filtered to yield a solid which is treated with alkaline water producing the hydroxy-protected mercaptan (Compound (7)) in the organic phase. This is converted to the activated form (Compound (8)) by treatment with methoxide in methanol. This is then reacted further as described below.

(b) 3-S-(1-Anhydro-D-ribofuranosyl)thiopropylamine

One equivalent of the compound of Example 10(a) (Compound (8)) freshly prepared is reacted with one equivalent of acrylonitrile to yield a thioether (Compound (9)). This is then reduced by treatment with LiAlH$_4$ in dry ether and the free deprotected amine (Compound (10)) is isolated by treatment with aqueous hydrochloric acid.

The corresponding aminopropylthioethers in which $R_1$ and $R_2$ are other than hydrogen are produced analogously, e.g. using the commercially available compounds (1) and (3) as starting materials.

EXAMPLE 11

Hapten Labelling

A 50 mmol/l solution of the compound of Example 10 in dimethylformamide (DMF) is diluted 1:5 (by volume) in 0.1 M bicarbonate solution (pH 9.2). To this solution, fluorescein isothiocyanate is added to a final concentration of 12 mmol/l. After 60 minutes incubation at ambient temperature, the fluorescein conjugate of the compound of Example 10 is purified by RPC using a Kromasil 100 Å C-18 column and a gradient mixture of 20 mM ammonium acetate (pH 7.0) and methanol.

EXAMPLE 12

Antigen Preparation

To a 1 mmol/l solution of the compound of Example 10 in 50 mmol/l phosphate, 125 mmol/l NaCl (pH 7.4) buffer, bovine serum albumin (BSA) is added to a final concentration of 5 mg/ml. To this mixture, bis(sulfosuccinimidyl) suberate is added to a final concentration of 1.2 mmol/l and the mixture is left to react for 60 minutes. The proteinaceous fraction, which includes the hapten-BSA conjugate, is isolated by size exclusion chromatography using a Pharmacia Superose 12 column with phosphate buffered saline as eluant.

EXAMPLE 13

Antibody Preparation

Antibodies to the compound of Example 10 are prepared analogously to Example 7 above using the antigen of Example 12. Antibodies not reactive with SAH and antibodies reactive with adenosine are rejected as preferably are antibodies reactive with homocysteine.

EXAMPLE 14

Hapten Production

N-Hydroxy succinimidyl 3-S-(1-Anhydro-D-ribofuranosyl)thiobutanoate

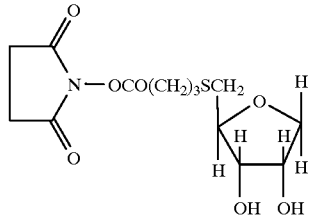

One equivalent of the compound of Example 10(a), freshly prepared, is reacted with 1 equivalent of ethyl 4-bromobutyrate to yield the ester compound (11). This is hydrolysed to the free acid by basic hydrolysis with aqueous sodium hydroxide in dioxane and deprotected by treatment with aqueous hydrochloric acid to yield the unprotected free acid (Compound (12)). One equivalent of this is mixed with two equivalents of N-hydroxysuccinimide in ice-cold dimethylformamide and to this is added 1.2 equivalents of dicyclohexylcarbodiimide under constant stirring. The reaction is allowed to proceed at ambient temperature for 18 hours, whereafter the mixture is cooled and ice-cold ether is added. The precipitated NHS-ester (Compound (13)) is recrystallized from DMF/ether, dried and then stored at 4° C. over a desiccant.

The corresponding NHS-esters in which $R_1$ and $R_2$ are other than hydrogen are produced analogously, e.g. using the commercially available compounds (1) and (3) as starting materials.

EXAMPLE 15

Hapten labelling

A 50 mmol/l solution of the compound of Example 14 in DMF is diluted 1:5 (by volume) in 0.1 M bicarbonate buffer (pH 9.2). To this solution, 5-aminoacetamido-fluorescein (fluoresceinyl glycine amide) as added to a final concentration of 12 mmol/l. After 60 minutes incubation at ambient temperature, the fluorescein conjugate of 3-S-(1-anhydro-D-ribofuranosyl)thiobutanoic acid is purified by RPC using a Kromasil 100 Å, C-18 column and a gradient mixture of 20 mM ammonium acetate (pH 7.0) and methanol.

EXAMPLE 16

Antigen Preparation

To a solution of BSA (5 mg/l in 50 mmol/l phosphate, 125 mmol/l NaCl (pH 7.4) buffer), the compound of Example 14 is added to a final concentration of 1 mmol/l. The mixture is left to react for 60 minutes and the proteinaceous fraction, which contains the BSA-hapten conjugate, is isolated by size exclusion chromatography using a Pharmacia Superose 12 column with phosphate buffered saline as eluant.

EXAMPLE 17

Antibody Preparation

Antibodies to the compound of Example 14 are prepared analogously to Example 7 above using the antigen of Example 12. Antibodies not reactive with SAH and antibodies reactive with adenosine are rejected as preferably are antibodies reactive with homocysteine.

EXAMPLE 18

Fluorescence Polarization Immunoassay

Enzyme Solution 50 mmol/l phosphate buffer (pH 7.4) containing 4 mg/ml casein, 120 mmol/l NaCl, and 10 U/l S-adenosyl-L-homocysteine-hydrolase.

Dithiothreitol (DTT)-solution

Dithiothreitol is dissolved in water to a concentration of 50 mmol/l and adjusted to pH 3.0 with HCl.

Adenosine-solution 1.8 mmol/l adenosine in 50 mmol/l phosphate buffer (pH 7.4).

Fluorescein-labelled SAH Solution 50 mmol/l phosphate buffer (pH 7.4) containing SAH conjugated to fluorescein, formed according to Example 6.

Antibody Solution

Monoclonal anti-SAH antibodies (e.g. according to Example 7) dissolved to a final concentration of 0.1 µmol/l in 50 mmol/l phosphate buffer (pH 7.4) containing 120 mmol/l NaCl and 1 mg/ml casein.

Assay Performance

Step 1

In a cuvette, 15 µl of sample, 10 µl enzyme solution and 10 µl adenosine solution are mixed with 10 µl of the acidic DTT-solution and kept at 37° C. for 15 minutes.

Step 2

To the cuvette, 100 µl of the fluorescein-labelled SAH solution and 1.0 ml of the antibody solution are added. With a spectrofluorometer equipped with a fluorescence polarization unit, the degree of polarization is measured as described in Example 7(c) (i) above and is plotted against the homocysteine concentration.

EXAMPLE 19

Fluorescence Polarization Immunoassay

Enzyme Solution 50 mmol/l phosphate buffer (pH 7.4) containing 1 mg/ml casein, 120 mmol/l NaCl, and 10 U/l S-adenosyl-L-homocysteine-hydrolase.

Dithiothreitol (DTT)-solution

Dithiothreitol is dissolved in water to a concentration of 50 mmol/l and adjusted to pH 3.0 with HCl.

Fluorescein-labelled SAH Solution/adenosine-solution 50 mmol/l phosphate buffer (pH 7.4) containing 10 µmol/l SAH conjugated to fluorescein, formed according to Example 6, and 1.8 mmol/l adenosine.

Antibody Solution

Monoclonal anti-SAH antibodies (e.g. according to Example 7) dissolved to a final concentration of 0.1 µmol/l in 50 mmol/l phosphate buffer (pH 7.4) containing 120 mmol/l NaCl and 1 mg/ml casein.

Assay Performance

In a cuvette, 10 µl plasma, 100 µl enzyme solution and 10 µl labelled SAH/adenosine-solution are mixed with 30 µl of the acidic DTT-solution and kept at 37° C. for 15 minutes.

After incubation, 1.0 ml of the antibody solution is added. With a spectrofluorometer equipped with a fluorescence polarization unit, the degree of polarization is measured as described in Example 7(c)(i) above and is plotted against the homocysteine concentration.

The assays of Examples 18 and 19 can also be performed using the labelled haptens and antibodies of Examples 11 and 13 or 15 and 17 in place of those of Examples 6 and 7.

EXAMPLE 20

Luminescence Assay

Assay Buffer I 50 mM Pipes-buffer (pH 6.6) containing 1 mg/ml casein, 10 mM DTT, 0.5 mM $MgCl_2$, and 30 mM KCl.

Assay Buffer II 40 mM Hepes-buffer (pH 7.75), 4 mmol/l EDTA, 20 mM magnesium chloride and 0.36 mmol/l DTT.

Assay Buffer III 40 mM Hepes-buffer (pH 7.75) containing 1.6 µg/ml luciferase (from *Photinus pyralis*), 700 µmol/l D-luciferin, 20 mmol/l magnesium chloride, 4 mmol/l EDTA, 0.36 mmol/l DTT and 0.3 mmol/l AMP.

Assay Procedure

To 130 µl of Assay buffer I is added 3 U of S-adenosyl-1-homocysteine hydrolase, 20 µl sample is added to this mixture and it is incubated for 15 minutes at 37 degrees Celsius. Thereafter, adenosine dissolved in Assay buffer I to a final concentration of $5 \times 10^{-6}$ mol/l is added. After 5 minutes incubation at 37° C., 750 µl of Assay buffer I containing $0.7 \times 10^{-5}$ mol/l ATP and 1 mU adenosine kinase are added, and the resulting solution is further incubated at 37° C. for 5 minutes. This solution is diluted 1:100 (by volume) with Assay buffer II and 500 µl of this diluted solution is immediately added to 500 µl of Assay buffer III. Both Assay buffers II and III were equilibrated to ambient temperature (21° C.). The luminescence produced is read in a photometer at 550 nm.

In parallel, an assay with no S-adenosyl-1-homocysteine hydrolase present is run. For clinical tests the homocysteine concentrations may be calculated by interpolation into a standard curve the difference in luminescence produced with and without S-adenosyl-1-homocysteine hydrolase present.

EXAMPLE 21

Polyclonal Antibody Preparation

Rabbit polyclonal antibodies to the antigens of Examples 12 and 16 are raised according to the protocol issued by the Dako Corporation, Copenhagen, Denmark. Polyclonal IgG is purified from the collected antiserum according to the same protocol. The polyclonal antibodies are purified from antibodies reactive with adenosine and homocysteine residues per se by passing the antibodies through Racti-Gel columns with immobilized adenosine and homocysteine residues (Gel and protocol as provided by Pierce Chemical Company, Belfium). Antibodies unreactive with SAH are also rejected. The selected antibodies can be used in the assays of the earlier Examples.

I claim:

1. In a method for assaying homocysteine in a sample, said method comprising the steps of (i) contacting said sample with a homocysteine-converting enzyme and (ii) assessing an analyte, wherein the improvement comprises in step (ii) without chromatographic separation assessing a non-labelled analyte selected from the group consisting of the homocysteine conversion products of the enzymic conversion of homocysteine by said enzyme.

2. The method as claimed in claim 1 wherein said sample is contacted with a second enzyme serving to convert said analyte and assessment of said analyte is effected indirectly by assessment either of a substrate of said second enzyme other than said analyte or of a product of enzymic conversion of said analyte by said second enzyme.

3. The method as claimed in claim 1 wherein said enzyme is S-adenosyl-homocysteine hydrolase and said analyte is S-adenosyl-homocysteine.

4. The method as claimed in claim 1 wherein said sample is a blood, plasma, or urine sample pretreated with a disulphide bond cleaving reducing agent.

5. The method as claimed in claim 1 wherein the assessment of said analyte is effected photometrically.

6. The method as claimed in claim 5 wherein said assessment is effected spectrometrically or colorimetrically.

7. The method as claimed in claim 5 wherein said assessment is effected turbidimetrically or nephelometrically.

8. The method as claimed in claim 6 wherein said assessment is effected using fluorescence polarization detection.

9. The method as claimed in claim 1 wherein assessment of said analyte is effected indirectly by detection of a chromophore or fluorophore on labelled S-adenosyl homocysteine or on a labelled furanose 6-thioether.

10. The method as claimed in claim 1 wherein a sample of blood, plasma or urine is treated with a reducing agent; the sample is contacted with adenosine and S-adenosyl-homocysteine hydrolase; the resultant mixture is incubated and then contacted with ATP and adenosine kinase and the mixture is incubated for at least one minute; the resulting mixture is contacted with luciferin and luciferase and light generated is detected.

11. An analytical kit for use in the assay of homocysteine in a sample by a method as claimed in claim 1, said kit comprising: a homocysteine converting enzyme; a signal forming agent; and, optionally, means for signal assessment.

12. The kit as claimed in claim 11 comprising in a first compartment inactive SAH-hydrolase and in a second compartment a reducing agent, whereby to produce on admixture of the contents of said first and second compartments activated SAH-hydrolase.

13. The kit as claimed in claim 12 wherein said second compartment comprises dithiothreitol in an acid medium.

* * * * *